(12) United States Patent
Higgs

(10) Patent No.: US 7,098,052 B2
(45) Date of Patent: Aug. 29, 2006

(54) DETECTION AND CLASSIFICATION OF MICRO-DEFECTS IN SEMI-CONDUCTORS

(75) Inventor: Victor Higgs, Hemel Hempstead (GB)

(73) Assignee: Aoti Operating Company, INC, Bend, OR (US)

(\*) Notice: Subject to any disclaimer, the term of this patent is extended or adjusted under 35 U.S.C. 154(b) by 29 days.

(21) Appl. No.: 10/469,536

(22) PCT Filed: Mar. 27, 2002

(86) PCT No.: PCT/GB02/01197

§ 371 (c)(1),
(2), (4) Date: Oct. 28, 2003

(87) PCT Pub. No.: WO02/077621

PCT Pub. Date: Oct. 3, 2002

(65) Prior Publication Data

US 2004/0092042 A1      May 13, 2004

(30) Foreign Application Priority Data

Mar. 27, 2001    (GB) .................................... 0107618

(51) Int. Cl.
*H01L 21/66*    (2006.01)
(52) U.S. Cl. ........................................................ 438/16
(58) Field of Classification Search .................. 438/16
See application file for complete search history.

(56) References Cited

U.S. PATENT DOCUMENTS 6,072,624 A * 6/2000 Dixon et al. ................. 359/385
6,200,823 B1 * 3/2001 Steffan et al. ................. 438/14
6,362,487 B1 * 3/2002 Ehlert et al. ............. 250/458.1

FOREIGN PATENT DOCUMENTS

WO    WO98 11425 A1    3/1998

OTHER PUBLICATIONS

"Non-Destructive, Non-Contacting Test of Si Wafers by Thermoreflectance," IBM Technical Disclosure Bulletin, vol. 29, No. 9, pp. 4105-4113, Feb. 1, 1987.*
Higgs et al., "Application of room temperature photoluminescence for the characterization of impurities and defects in silicon", Proceedings of the SPIE, vol. 3895, pp. 21-37 (Sep. 13, 1999).
Ribes et al., "Refelected-light photoluminescence and OBIC imaging of solar cells using a confocal scanning laser MACROscope/microscope", Solar Energy Materials and Solar Cells, Elsevier Science Publishers, vol. 44, No. 4, pp. 439-450 (Dec. 15, 1996).
Bothe et al., "Spatially-resolved photoluminescence measuerments on Cu(In, Ga)Se2 thin films", Thin Solid Films, vol. 403-404, pp. 453-456 (Feb. 1, 2002).

\* cited by examiner

*Primary Examiner*—Stephen W. Smoot
(74) *Attorney, Agent, or Firm*—Jacobson Holman PLLC

(57) ABSTRACT

A method and apparatus for the detection and classification defects in a silicon or semi-conductor structure, in particular using room temperature photoluminescence effects, is described. The method involves directing a high intensity beam of light at a surface of a sample of silicon or semi-conductor structure to be tested producing a photoluminescence image, producing a reflected light image, combining the information in the two images to detect, map and identify and/or characterize micro-defects in the silicon or semi-conductor structure.

11 Claims, 5 Drawing Sheets

PL Map

Surface Map

PL Map

Surface Map

PL Map

Surface Map

PL Map

Surface Map a) b)

PL Map                    Surface Map

PL Map                                    Surface Map

PL Map                                    Surface Map

PL Map    Surface Map

DETECTION AND CLASSIFICATION OF MICRO-DEFECTS IN SEMI-CONDUCTORS

The invention relates to an apparatus and method for detection and classification of micro-defects in semiconductors or Silicon structures and particularly, but not exclusively, in Silicon on insulator wafers, polycrystalline Silicon, SiGe epilayers and like structures.

Rapidly shrinking device geometry and technological demand for high-performance circuits impose great demands to understand the physical phenomena related to microstructural properties of materials. Understanding these properties is necessary to facilitate the reduction in both, number of defects in the material and their degrading impact on IC performance and yield. All Silicon wafers contain certain level of defects whose nature and density, depend upon crystal growth conditions and thermal history of the wafer in subsequent processing. Silicon on insulator fabrication techniques introduce their own category of defects, some being common and some being specific to the method of fabrication. To succeed in material improvement it is important to understand impact of process conditions on formation of defects, defects nature and their effects on device characteristics.

Defects are encountered in Silicon-on-insulator (SOI) materials fabricated using separation by implantation of oxygen (SIMOX). Wafers produced by this method have defect types specific defect type in SIMOX, such as Silicon bridges and Silicon inclusions in the buried oxide part of the structure (BOX). This invention can be used to locate and characterise the nature of these defects.

Polycrystalline Silicon contains grain boundaries (i.e. the boundary between two crystal regions of different orientation) which are physical defects. On the sample surface these defects will also have electrical activity affecting the behavior of the material. This invention can be used to locate and characterise the nature of these defects.

Developments in crystal growth have enabled the production of Silicon wafers free from dislocation. However, dislocation free wafers may not be able to remain this way after the wafers are subjected to high temperature processing. Defects formed within the device active region in the wafer and defects produced in the gate oxide generally degrade device performance, lead to yield losses and reliability problems. This invention can be used to locate and characterise the nature of these defects.

Transition metals, which are fast diffusers in Silicon, readily form deep levels, i.e. away from the valance or conduction band edge, and also lead to decoration of both point and extended defects which eventually lead to device failure. These transition metal impurities also form recombination centres and traps which can dramatically reduce carrier lifetime and can also act as dark current generation sites, i.e. in the absence of light, charge leakage will occur. Gettering techniques, where mechanical damage, such as abrasion, is typically undertaken in order to provide a damaged site, which effectively acts as a sponge soaking up impurities in the wafer, have been developed to remove transition metal impurities from the device active areas. It therefore follows that the aforementioned damage is deliberately targeted to an area in the wafer remote from the electrical device. Thus internal gettering techniques introduce defects in the Silicon substrate which attract unwanted impurities away from the device areas. Gettering sites need to be characterised to control their distribution for different process conditions, a task which can be performed with the present invention.

Epitaxial Silicon, that is the deposited uppermost layers of Silicon, typically in the order of microns thick, has been used to overcome problems with as-grown CZ wafers. In other words, as the thickness in the epitaxial Silicon increases, given that this layer can be grown in a defect-free manner, it can be used as a site for the electric device without fear of contamination in the bulk wafer affecting the activity of the device. However it is not always possible to use an epitaxial layer of sufficient thickness for this activity and where the epitaxial layer is thin then defects in the bulk wafer can interfere with the electrical device. Moreover, epitaxial layers suffer from problems of metal contamination.

Several techniques already exist for the detection of defects in as-grown material, these include wet chemical etching in order to reveal flow pattern defects; light scattering topography where the topography of the surface wafer is examined using light to detect undulations which in turn are indicative of defects in the sub-structure; and transmission interference contrast microscopy where the transmission of light through the wafer is examined and the phase shift due to small path changes is used to image defects in the wafer. All of these techniques are used to measure the physical presence of defects in the wafer. However they do not measure the electrical properties of the defects and moreover in some cases they are destructive. Accordingly, as techniques for determining the structural integrity of a wafer they are lacking in terms of the information they provide and moreover they can be positively destructive.

Photoluminescence (PL) spectroscopy is a very sensitive technique for investigating both intrinsic and extrinsic electronic transitions at impurities and defects in semiconductors. When silicon is excited at low temperatures with laser irradiation above the band-gap of the material, electron hole pairs are produced. These carriers can recombine in various different ways. some of which give rise to luminescence. The electron hole pairs formed at low temperature can be trapped at impurities in Silicon and they emit photons characteristic of this interaction, thereby giving impurity specific information in the photoluminescence spectra. There are a significant number of applications of PL spectroscopy to Silicon including characterization of Silicon after different processing steps, characteristic of device fabrication for example implantation, oxidation, plasma etching, the detection of point defect complexes and the presence of dislocations. One of the most important applications includes the non-destructive measurement of shallow donors and acceptors such as arsenic, boron and phosphorous. Notably, this technique enables the measurement of the concentration of these shallow donors and acceptors. However, in conventional applications in order to obtain this spectral information and unambiguous chemical identification of the optical centres, measurements need to be carried out at liquid helium temperatures. It is known throughout the industry that at room temperature the PL signal is significantly weakened and very little useful spectral information can be obtained.

International patent application WO97/09649 describes a non-destructive technique which makes practical the detection of electrically active defects in semi-conductor structures based on room temperature PL. The patent application discloses a PL technique which has industrial application in that it enables the image to be produced within minutes and which has a further added advantage in producing micro imaging of small individual defects particularly near to the surface of the wafer, where the device is fabricated.

The technique provides information concerning defects in a semiconductor or Silicon structure at a rate appropriate to industrial use and in particular enables us to visualise defects in the upper regions of the semiconductor or Silicon structure and in particular near to the surface of same. The technique exploits enhanced non radiative recombination of electron hole pairs at defects in a semiconductor or Silicon structure with a view to enhancing contrast in a PL image of said semiconductor or Silicon structure so as to enhance the viewing of defects in same.

The technique detects and allows high resolution imaging of certain electrically active micro defects on a highly accurate scale. However, it does not detect all relevant defects, since some produce little photoluminescence at room temperature. It does not distinguish between different defects with similar electrical activity, whereas in practice the identity of the particular defect can be critical in deciding whether it will have an unacceptably detrimental effect on the resultant semi-conductor structures.

It is an object of the invention to mitigate some or all of these disadvantages in prior art room temperature PL techniques.

It is a particular object of the invention to develop and adapt prior art room temperature PL techniques and apparatus such as that described above so that effective identification of defects and/or classification of defect types is also made possible.

It is a particular object of the invention to develop room temperature PL techniques and apparatus exploiting room temperature PL which allow the accurate imaging and characterization of micro-defects in SOI and especially SIMOX and bonded wafers, in polycrystalline Silicon, and in SiGe and like epilayers.

Thus, according to the invention in its broadest aspect, a method for the detection and classification defects in a Silicon or semi-conductor structure comprises:

directing a high intensity beam of light such as a high-intensity laser at a surface of a sample of Silicon or semi-conductor structure to be tested;

producing a first photoluminescence image from photoluminescence produced by excitation of the Silicon or semi-conductor structure by the light beam;

producing a second reflected light image from light reflected from the surface of the Silicon or semi-conductor structure from the light beam;

combining the information in the said two images to detect, map and identify and/or characterise micro-defects in the Silicon or semi-conductor structure.

In its broadest aspect the invention is based on collecting room temperature photoluminescence and reflected laser light image data from a semiconductor or Silicon structure under selected excitation conditions, and then comparing the data to characterise as well as map defects.

When a semiconductor material is excited by above band illumination electrons and holes are generated, recombination back to equilibrium can take place radiatively to produce light (photoluminescence) PL or non-radiatively producing heat. These two processes are in direct competition; in a indirect band material (such as Si) the non-radiative process is faster and more efficient. The non-radiative process is increased by defects and deep level impurities. The photoluminescence emission process is reduced or quenched at the location of a defect or contaminated region. Focusing a laser beam onto a semiconductor surface and then collecting the PL signal can therefore be used to monitor the presence of defects.

By collecting both the PL and reflected laser light images (surface map=SM) information can be obtained about the defect characteristic and can also be used classify the defect type. This relies on the fact that the response of different defects differs in the two scenarios. In particular the PL technique detects electrically active defects, which may or may not affect reflected laser light intensity, whilst the direct reflected laser image shows defects, which may or may not be electrically active.

Comparison of the results with suitable predetermined reference information about defects or defect types allows the detected defects to be identified or characterised much more accurately than using PL alone to produce results of much enhanced practical value. The two images may be coprocessed to produce a defect map which both locates and characterises the defects for subsequent assessment of their likely detrimental impact on the structure.

Examples of this method are shown in FIGS. 1–3 for Si wafers. In FIG. 1 the defects only appear in the PL image because they quench the PL signal at the location of the defect and are called electrically active. Such defects will degrade device performance if it is fabricated where the defects are located. The defect observed in FIG. 2 is a surface scratch it is observed in both the PL and surface map images. FIG. 3 shows the image of surface particles which appear on both the PL and SM images.

Combination of the first and second images may be merely by simultaneous observation. Preferably however the images are analysed statistically, for example by digitizing prior to performing a numerical comparison/analysis.

Preferably, the method involved generating a digitized intensity measurement (e.g. point by point reading but preferably a digitized intensity map) representative of the intensity of the first, PL image; generating a digitized intensity measurement (e.g. point by point reading but preferably a intensity digitized map) representative of the intensity of the second, SM image; numerically comparing the digitized intensity measurements to produce a combined result; comparing the combined result with reference data about defect behavior to characterize the defects detected.

The PL signal generated as a result of laser excitation is given by $$I = (1-R)C \int_V A(z)\eta \frac{p(z)}{\tau} dz \qquad [1]$$

where V is the volume of the sample, $\eta$ is the internal quantum efficiency ($\tau/\tau_{nrad}$) and p(z) is the excess carrier density due to optical excitation. C denotes the collection and detector efficiency, and A and R are the correction factors that account for absorption and reflection losses in the sample. The variation in PL intensity recorded in a PL map, reveals variations in $\tau$. This can be produced by variations in either the total recombination rate $\tau$, or the radiative rate $\tau_{rad}$. In general in Si, $\tau$ is approximately equal to the non-radiative lifetime $\tau_{nrad}$, and if we assume that as the beam is scanned across a defect, there is a spatial variation in $\tau_{nrad}$ only, this will change $\tau$ also. Experimentally it has been demonstrated that the PL signal change is directly related to changes in $\tau$. Therefore the excess carrier distribution at the defect is different to that in the defect free material and defects can thereby be detected.

Photoluminescence is thus collected from the Silicon or semi-conductor structure so as to visualise and observe defects in same by production of an image, in which non-radiative recombination of electron pairs is detected as darkened regions in the image at the physical position of the defect. Reflected laser light is similarly collected from the Silicon or semi-conductor structure so as to visualise and observe defects in same by production of an image in which unreflected light from a defect site is detected as darkened regions in the image at the physical position of the defect.

Certain types of defect can modify the excitation density of electrons and holes produced by the excitation laser, this can be caused by scattering or reflection. This will also lead to a variation in the PL signal (factors A and R in equation 1). Preferably the method correct for this. Preferably a digitized intensity measurement (such as a point by point reading but preferably a digitized intensity map) representative of the intensity of the PL image is generated by applying an appropriate numerical correction factor to collected absolute intensity data to correct for such variations in excitation density before comparison with the SM intensity data.

In the preferred embodiment, a software algorithm is used that corrects the PL image for variations in excitation density. To do this we use the signal variation detected in the SM image to correct the PL image.

This correction takes the ranges of the PL and Surface intensity data and divides the PL range by the SM. This is then multiplied by surface variation from its average value using the standard deviation (s.d) to factorize this conversion.

The resultant value can then be added to the PL intensity data to give the new PL intensity data for comparison with SM intensity data, and in particular to give a corrected PL intensity map for comparison with the SM map.

$$\left[\frac{PLrange}{SMrange} \times SMs.d \times (SM - AveSM)\right] + PL$$

Defects are type-characterized or identified by comparing intensity, in particular digitized intensity data from intensity maps, relating to the PL and surface map (in particular the PL data corrected as above and the surface map) and referring to a set of reference data for particular defect types.

High injection level conditions are preferably used in the method of the invention to produce the PL image and defects are detected due to the local change in carrier lifetime at the defect. These defects are typically observed as darkened regions at the physical position of the defect, but in some instances enhanced radiative recombination gives rise to relatively lightened regions having regard to the background. The recombination at the defects is enhanced by increasing the injection level so that it is not limited by the availability of minority carriers. The preferred PL technique is that in WO97/09649 incorporated herein by reference.

The success of the room temperature PL method disclosed therein is, in part, due to the probing volume of the laser being small, spatial resolution preferably 0.1–20 µm, ideally 2–5 µm, and with a peak or average power density of between $10^4$–$10^9$ watts/cm$^2$, so that localised defects have much greater effect on the measured PL intensity and is also believed, in part, because since the excitation is focused the injected carrier density is high. This greatly increases the probability of non-radiated recombination at the defect and hence physical location of the defect. The present invention exploits this, but also applies further imaging information to produce a much more useful overall map of the defects than using PL alone.

Reference herein to a high-intensity laser is meant to include, without limitation, a high power density laser i.e. where regardless of the power of the laser the emittance is focused.

In a preferred method of the invention a pulsed laser excitation source is used and ideally luminescence data is measured and/or the luminescence images collected as a function of time. This means that both depth and spatial resolution are improved and can be used to obtain information on the carrier capture cross sections of the defects. Time resolved measurements can also be used to measure the effective carrier lifetime and obtain lifetime maps.

In a further embodiment of the invention confocal optics are used to obtain depth discrimination of the defects by exciting a large volume of said semiconductor with a laser and collecting images from a series of focal planes.

The method is particularly effective when applied in detecting imaging and characterising near surface microdefects in SOI and especially SIMOX and bonded wafers, in polycrystalline Silicon, and in SiGe and like epilayers.

Digitization of image intensity information and/or application of correction factors to PL image data and/or numerical comparison of digitised PL and SM image data and/or comparison of the results thereof with reference data may be implemented by suitable computer software.

According to further aspects, the invention comprises computer software to implement the said method steps of digitization of image intensity information and/or application of correction factors to PL image data and/or numerical comparison of digitised PL and SM image data and/or comparison of the results thereof with reference data; such software on a suitable data carrier, said data carrier optionally further incorporating said reference data; and a suitably programmed computer programmed with such software and optionally further programmed with said reference data.

According to a further aspect of the invention there is provided an apparatus for undertaking photoluminescence imaging of a semiconductor or Silicon structure simultaneously or consecutively with reflected light imaging to perform the above method.

The apparatus comprises a high intensity light beam source such as a high-intensity laser directable at a surface of a sample of Silicon or semi-conductor structure to be tested; a first imaging means to produce a first image from photoluminescence produced by excitation of the Silicon or semi-conductor structure by the light beam; a second imaging means to produce a second reflected light image from light reflected from the surface of the Silicon or semi-conductor structure; means to enable comparison of the two images.

The imaging means may simply be displays (direct screen, photographic, camera and screen etc) allowing simultaneous viewing by an observer.

Additionally or alternatively, digital imagers such as digital cameras collect digitised image intensity data to be processed numerically as above described.

The apparatus preferably further comprises means to process digitised image intensity data. In particular it further comprises a first data register to store digitised image intensity data from PL imaging, a second data register to store digitised image intensity data from RL imaging, a reference register containing intensity data characteristic of defect type, optionally a data corrector to apply correction to data in the first register using data in the second register as above described, an image comparator to combine data from the first and second registers to produce a combined result and to compare the a combined result with data in the reference register to characterise defects, a display to display the detected and characterised defect results.

In a preferred embodiment of the invention the laser is modulatable so as to adjust the wavelength excitation of same thereby enabling a user of said apparatus to sample said semiconductor or Silicon structure at different depths. For example, a short wavelength may be used to sample near the surface of the said semiconductor or structure and a longer wavelength to look deeper into the semiconductor or structure.

In yet a further preferred embodiment of the invention the apparatus is provided with means to enable pulsing of said laser and ideally also to PL images to be obtained as a function of time.

In a yet further preferred embodiment of the invention said apparatus is provided with means for modulating said laser at high frequencies (0.1–100 MHz) thereby enabling a user of said apparatus to sample said semiconductor or Silicon structure at different depths.

In yet a further preferred embodiment of the invention said apparatus comprises a laser of a spot size of between 0.1 mm and 0.5 microns and/or a power density of between $10^4$ to $10^9$ watts/cm$^2$.

In yet a further preferred embodiment of the invention the apparatus comprises confocal optics which is used to obtain depth discrimination of the defects by exciting a large volume of said semiconductor with a laser and collecting images from a series of focal planes.

According to a further aspect the invention comprises PL and SM images and/or PL and SM digitised intensity maps of a silicon or semi-conductor structure generated in viewable and/or digitally processable form by the foregoing method or using the foregoing apparatus and suitable for comparison to detect, map and identify and/or characterise micro-defects in the silicon or semi-conductor structure.

The invention is illustrated with reference to FIGS. 1 to 10 of the accompanying drawings in which.

Figure 1:
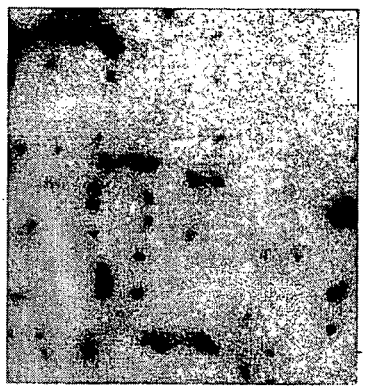
FIG. 1 shows PL and surface maps produced in accordance with the invention illustrating electrically active defects.
Figure 1:
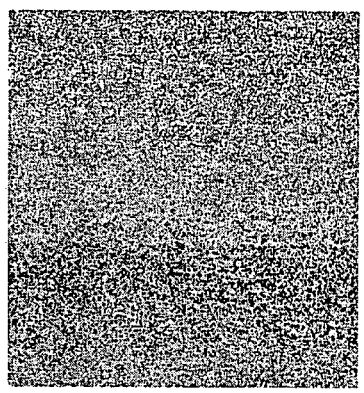
Figure 2:
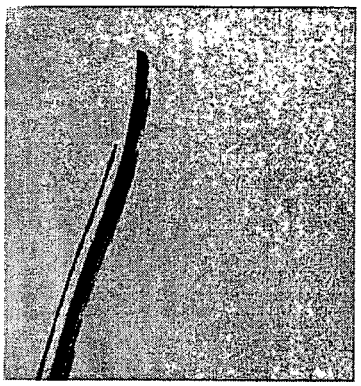
FIG. 2 shows PL and surface maps produced in accordance with the invention illustrating a surface scratch.
Figure 2:
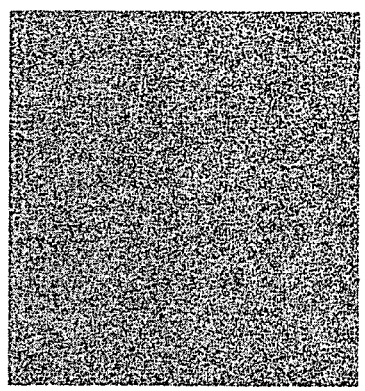
Figure 3:
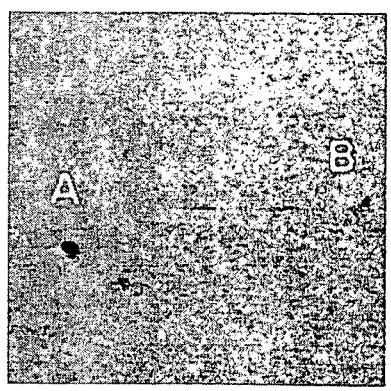
FIG. 3 shows PL and surface maps produced in accordance with the invention illustrating surface particles.
Figure 3:
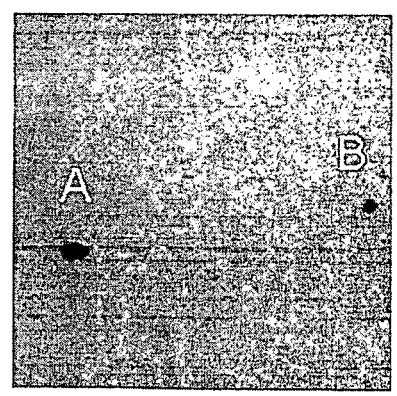

FIGS. 1 to 3 show silicon wafers. In FIG. 1, the defects only appear in the PL image because they quench the PL signal at the location of the defect and are called electrically active. Such defects will degrade device performance if it is fabricated where the defects are located. The defect observed in FIG. 2 is a surface scratch it is observed in both the PL and surface map images. FIG. 3 shows the image of surface particles which appear on both the PL and surface map.

Figure 4:
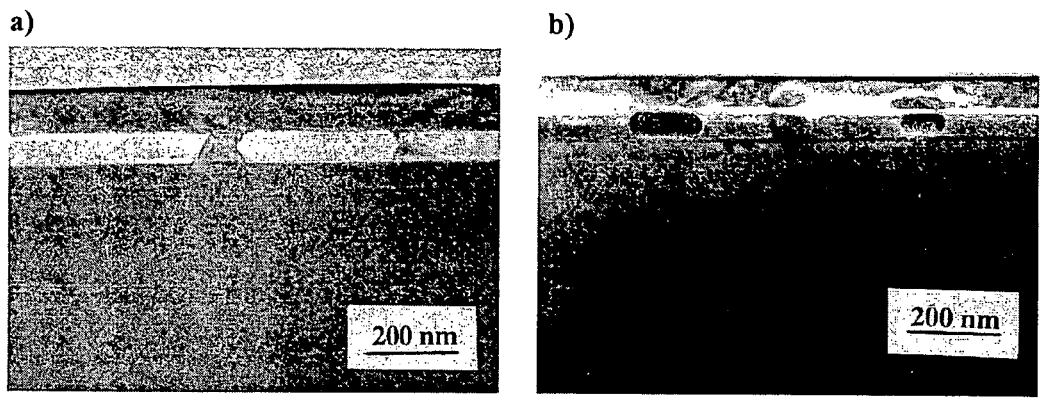
FIG. 4 shows TEM cross-section micrographs showing a) Silicon bridges. b) and Si inclusions.

PL maps have been measured on Silicon-on-insulator (SOI) fabricated using separation by implantation of oxygen (SIMOX). To illustrate the usefulness of this method wafers were produced deliberately to have specific defect type in SIMOX, Silicon bridges and Silicon inclusions in the buried oxide part of the structure (BOX). High-resolution transmission electron microscopy (TEM) was used to identify the different defects. FIG. 4a shows a cross section TEM image representative of the defects detected in the sample with Si bridges. The sample containing Si inclusions is shown in FIG. 4b.

Figure 5:
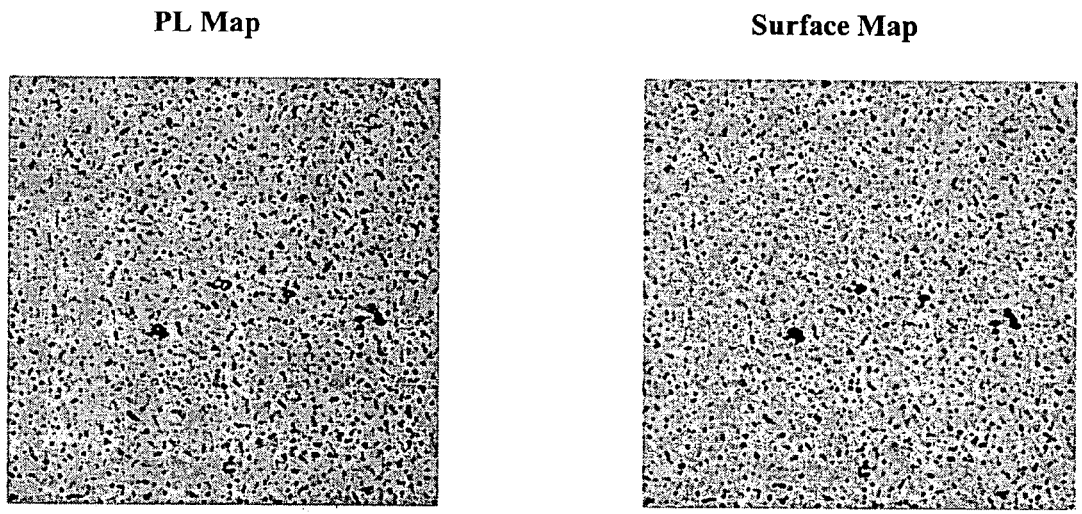
FIG. 5 shows PL and surface maps produced in accordance with the invention illustrating a SIMOX wafer containing Si bridging defects.

The PL image of the sample containing Si bridges is shown in FIG. 5, after software correction. The individual defects are detected as small localized areas of reduced PL intensity, each black spot corresponding to a Si bridge defect. The PL image from the sample containing Si inclusions shows localized areas of increased PL intensity. Each individual defect relating to a Si inclusion. After acquiring the PL image from these well known defect types and correcting the, PL image it is now possible to classify the defect type by the effect on the PL signal at the defect. Thereby allowing classification and enabling defect detection.

Figure 6:
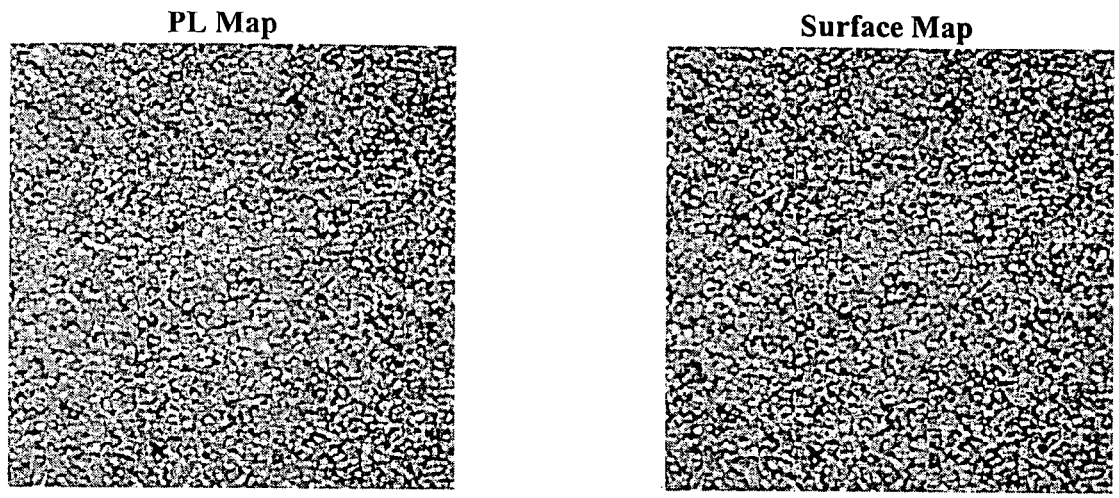
FIG. 6 shows PL and surface maps produced in accordance with the invention illustrating a SIMOX wafer-containing Si inclusions.

This software procedure can be applied to other defects detected in SOI structures. For SOI wafers fabricated using direct wafer bonding, defects can be formed where the wafers do not bond are termed voids. An example of this type of void defect detected by PL is shown in FIG. 6. The PL image is corrected and different type of void defects can be classified. These voids can be produced by particles, surface roughness or contamination.

Figure 7:
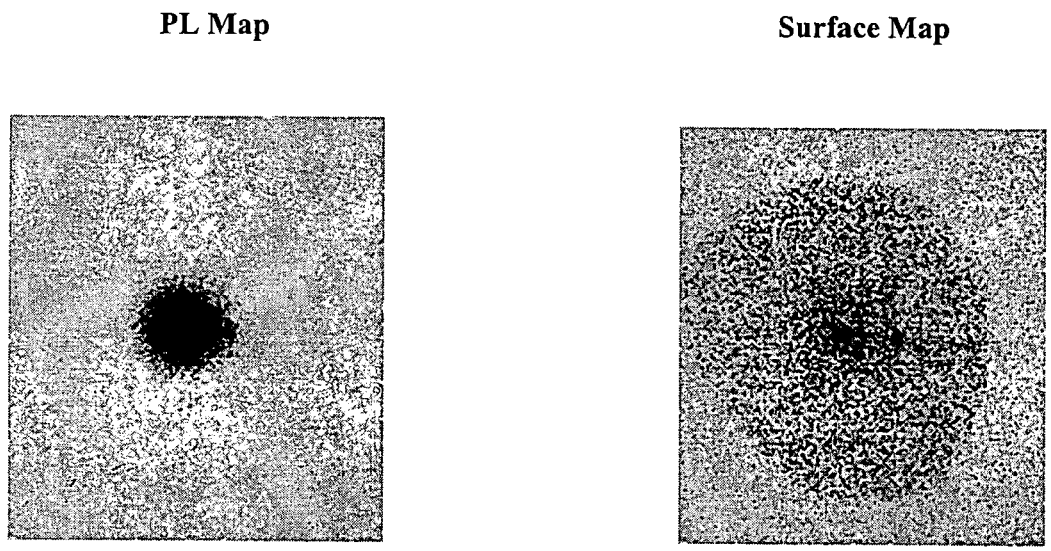
FIG. 7 shows PL and surface maps produced in accordance with the invention illustrating SOI void defect in bonded wafers.
Figure 8:
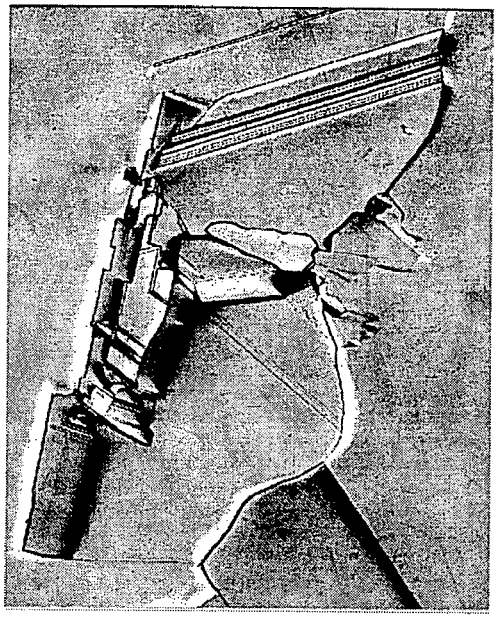
FIGS. 8 and 9 show PL and surface maps produced in accordance with the invention illustrating defects in polycrystalline Si.
Figure 8:
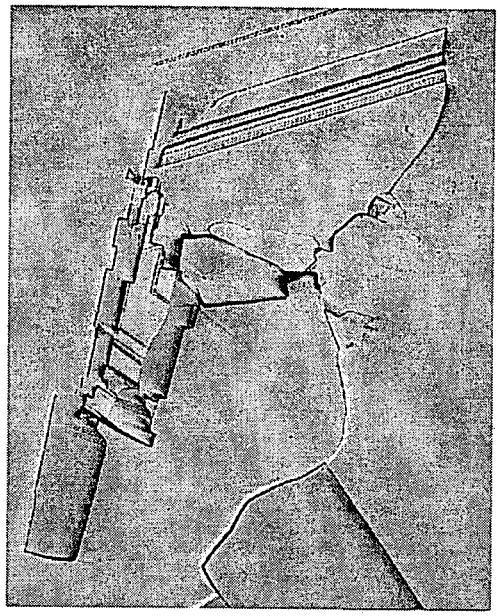

Polycrystalline Si contains grain boundaries (is the boundary between two crystal regions of different orientation) which are physical defects on the sample surface these defects will also have electrical activity, to remove the physical effect of the boundary we have applied the software correction model to correct the PL images the results are shown in FIGS. 7 and 8. This allows the electrically nature of the grain boundaries and inter-grain defects to be assessed and classified.

Figure 9:
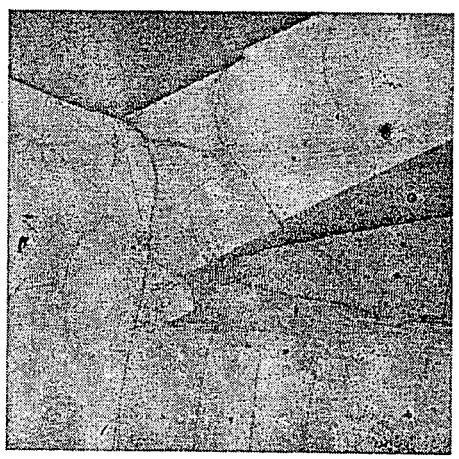
Figure 9:
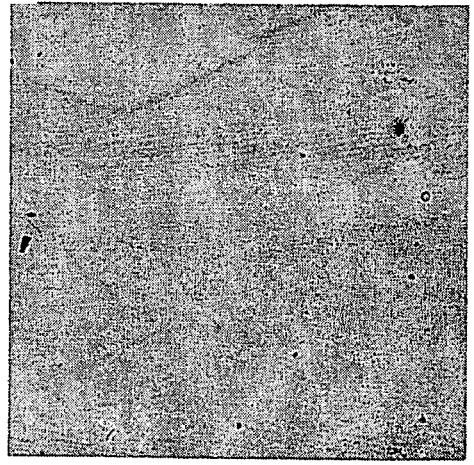
Figure 10:
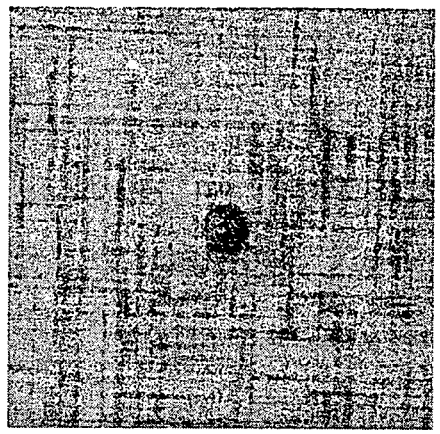
FIG. 10 shows PL and surface maps produced in accordance with the invention illustrating defects in SiGe epilayer.
Figure 10:
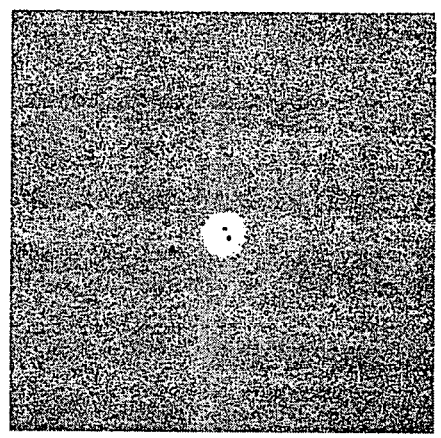

Defects can also be detected in SiGe epilayers; a PL map of a typical defect is shown in FIG. 9. Clearly, again the software correction can be used to facilitate classification of the defect type.

The application of PL mapping coupled together with the reflected surface map can be used for correcting the PL image to reveal the true electrical activity and enables defect classification.

The invention claimed is:

1. A method for the detection and classification of defects in a silicon or semi-conductor structure comprising the steps of:

directing a high intensity beam of light at a surface of a sample of silicon or semi-conductor structure to be tested;

producing a first photoluminescence ("PL") image from photoluminescence produced by excitation of the silicon or semi-conductor structure by the light beam;

producing a second reflected light ("SM") image from light reflected from the surface of the silicon or semi-conductor structure from the light beam;

combining information in the said two images wherein said two images are analyzed statistically by digitizing and co-processing by performing the steps of generating a digitized intensity measurement representative of the intensity of the first, PL image; generating a digitized intensity measurement representative of the intensity of the second, SM image; numerically comparing the digitized intensity measurements to produce a combined result; comparing the combined result with reference data about defect behavior to characterize the defects detected to produce a defect map whereby the detected defects are both mapped spatially and identified or characterized.

2. The method of claim 1 wherein one or both of the generated digitized intensity measurements is produced as an intensity digitized spatial map.

3. The method of claim 1 further comprising correcting the PL digitized intensity measurement for excitation density modification associated with certain defects by applying an appropriate numerical correction factor to collected absolute intensity data to correct for such variations in excitation density before comparison with the SM digitized intensity measurement data.

4. The method of claim 3 wherein a software algorithm is used to correct the PL image for variations in excitation density.

5. The method of claim 3 wherein correction is effected by evaluating the measured intensity ranges of the PL and Surface maps, dividing the PL range by the SM range, multiplying this result by surface variation from its average value using the standard deviation (s.d) to factorize this conversion, adding the resultant value to the collected absolute PL intensity data to give new PL intensity data.

6. The method of claim 1 comprising directing a high-intensity laser at a surface of the sample at room temperature.

7. The method of claim 6 wherein the probing volume of the laser is small, spatial resolution being between 0.1–20 µm.

8. The method of claim 7 wherein the spatial resolution is between 2 and 5 µm.

9. The method of claim 7 wherein the peak or average power density is between $10^4$–$10^9$ watts/cm$^2$.

10. The method of claim 1 wherein a pulsed laser excitation source is used and luminescence data is measured and/or the luminescence images collected as a function of time.

11. The method of claim 1 wherein confocal optics are used to obtain depth discrimination of the defects by exciting a large volume of said semiconductor with a laser and collecting images from a series of focal planes.

* * * * *